US012653765B2

(12) United States Patent
Iwami et al.

(10) Patent No.: US 12,653,765 B2
(45) Date of Patent: Jun. 16, 2026

(54) SUNSCREEN COSMETIC

(71) Applicant: Shiseido Company, Ltd., Tokyo (JP)

(72) Inventors: Shiho Iwami, Tokyo (JP); Yurika Watanabe, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 882 days.

(21) Appl. No.: 17/785,697

(22) PCT Filed: Dec. 16, 2020

(86) PCT No.: PCT/JP2020/046913

§ 371 (c)(1),
(2) Date: Jun. 15, 2022

(87) PCT Pub. No.: WO2021/125212

PCT Pub. Date: Jun. 24, 2021

(65) Prior Publication Data

US 2023/0053779 A1     Feb. 23, 2023

(30) Foreign Application Priority Data

Dec. 16, 2019     (JP) ................................. 2019-226164

(51) Int. Cl.
| | |
|---|---|
| *A61K 8/25* | (2006.01) |
| *A61K 8/02* | (2006.01) |
| *A61K 8/73* | (2006.01) |
| *A61K 8/92* | (2006.01) |
| *A61Q 17/04* | (2006.01) |

(52) U.S. Cl.
CPC ................ *A61K 8/25* (2013.01); *A61K 8/022* (2013.01); *A61K 8/732* (2013.01); *A61K 8/922* (2013.01); *A61Q 17/04* (2013.01); *A61K 2800/412* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 5,188,831 A | 2/1993 | Nicoll et al. | |
| 5,256,404 A | 10/1993 | Martino et al. | |
| 7,329,719 B2 | 2/2008 | Pavlin | |
| 2006/0280714 A1 | 12/2006 | Maningat et al. | |
| 2013/0343801 A1 | 12/2013 | Sakuma et al. | |
| 2014/0105943 A1* | 4/2014 | Pistorio ................. | A61K 8/927 424/47 |

| | | | |
|---|---|---|---|
| 2016/0143831 A1 | 5/2016 | Brock et al. | |
| 2017/0135920 A1 | 5/2017 | Enomoto et al. | |
| 2017/0312199 A1 | 11/2017 | Shah et al. | |

FOREIGN PATENT DOCUMENTS

| | | |
|---|---|---|
| EP | 1 421 931 A2 | 5/2004 |
| EP | 3 437 625 A1 | 2/2019 |
| EP | 3 636 245 A1 | 4/2020 |
| JP | 2003-095872 A | 4/2003 |
| JP | 2006-342322 A | 12/2006 |
| JP | 2007-217361 A | 8/2007 |
| JP | 2013-136493 A | 7/2013 |
| JP | 2013-209303 A | 10/2013 |
| JP | 2014-004084 A | 1/2014 |
| JP | 2014-019688 A | 2/2014 |
| JP | 2018-087146 A | 6/2018 |
| JP | 2018-162243 A | 10/2018 |
| JP | 2019-073474 A | 5/2019 |
| WO | WO-2011/061864 A1 | 5/2011 |
| WO | WO-2014/060405 A2 | 4/2014 |
| WO | WO-2014/203913 A1 | 12/2014 |
| WO | WO-2016/184419 A1 | 11/2016 |
| WO | WO-2017/112982 A1 | 7/2017 |
| WO | WO-2018/225768 A1 | 12/2018 |

OTHER PUBLICATIONS

Google translation JP 2007-217361 A, printed 2025 (Year: 2025).
Google translation JP 2013-136493 A, printed 2025 (Year: 2025).
Google translation JP 2014-019688 A, printed 2025 (Year: 2025).
Google translation EP 1,421,931 A2, 14 pages, printed 2026 (Year: 2026).
Google translation EP 3,437,625 A1, 13 pages, printed 2026 (Year: 2026).
Google translation JP 2018-087146 A, 12 pages, printed 2026 (Year: 2026).
Google translation WO 2016/184419 A1, 5 pages, printed 2026 (Year: 2026).
USPTO artificial intelligence top results, 2 pages, printed 2026 (Year: 2026).

* cited by examiner

*Primary Examiner* — Nannette Holloman
(74) *Attorney, Agent, or Firm* — Foley & Lardner LLP

(57) ABSTRACT

An objective of the invention is to provide a sunscreen cosmetic that, by blending an environmentally friendly and highly water-resistant powder component instead of microplastic beads or silica, can achieve high ultraviolet protection power even when a small amount of an ultraviolet protectant is used, that moreover has the property wherein, by coming into contact with water, perspiration or the like, the ultraviolet protection effects are increased even more than those directly after being applied, and that also has an excellent texture. The sunscreen cosmetic according to the present invention contains (A) an oil phase thickener, (B) an ultraviolet protectant, and (C) a wax powder having a volume-average particle size of 1 to 30 μm.

7 Claims, No Drawings

SUNSCREEN COSMETIC

CROSS-REFERENCE TO RELATED APPLICATIONS

This application is the U.S. National Stage of PCT/JP2020/046913, filed Dec. 16, 2020, which claims priority to JP 2019-226164, filed Dec. 16, 2019.

TECHNICAL FIELD

The present invention relates to a sunscreen cosmetic. More specifically, the present invention relates to a sunscreen cosmetic that can achieve high ultraviolet protection power, even without blending a large amount of an ultraviolet protectant, by blending an oil phase thickener and a prescribed wax powder, that moreover has the property wherein, by coming into contact with water, perspiration or the like, the ultraviolet protection effects are increased even more than those directly after being applied, and that also has an excellent texture.

BACKGROUND ART

Protecting the skin from damage due to ultraviolet rays is an important problem in skin care and body care, and various UV-care cosmetics for minimizing the harmful effects of ultraviolet rays on the skin have been developed. Sunscreen cosmetics, which are a type of UV-care cosmetic, are cosmetics that are intended to protect the skin from damage due to ultraviolet rays by covering the skin with a coating film in which an ultraviolet protectant such as an ultraviolet absorbing agent or an ultraviolet scattering agent is blended, thereby absorbing or scattering UVA and UVB rays, and limiting the amount of ultraviolet rays that reach the skin (Non-Patent Document 1).

Ultraviolet absorbing agents are blended into many sunscreen cosmetics for being able to obtain high ultraviolet protection effects, having good compatibility with skin and being resistant to sweat and water. However, among ultraviolet absorbing agents, there are those that generate heat or undergo chemical changes when absorbing ultraviolet rays, thereby causing redness or itchiness on the skin, and further causing allergies. For example, ethylhexyl methoxycinnamate (octyl methoxycinnamate) has conventionally been commonly used in sunscreen cosmetics as a representative ultraviolet absorbing agent that absorbs UVB. However, it can cause strain for users with sensitive skin. Patent Document 1 proposes blending a dimethyl ether into an external skin-care preparation in order to alleviate irritation due to ethylhexyl methoxycinnamate.

Additionally, many ultraviolet absorbing agents are solid at ambient temperature, and stably dissolving these into cosmetics without precipitation requires a suitable amount of oil. For this reason, in order to blend a large amount of ultraviolet absorbing agents, the oil amount must also be increased, and the oils can cause stickiness and degrade the feeling in use. Therefore, a water-soluble ultraviolet absorbing agent is sometimes blended instead of blending a large amount of an oil-soluble ultraviolet absorbing agent. However, in general, water-soluble ultraviolet absorbing agents tend to have inferior ultraviolet protection power in comparison with those that are oil-soluble, and it is difficult to achieve sufficient ultraviolet protection power even when a large amount of a water-soluble ultraviolet agent is blended. Additionally, in the case in which a water-soluble ultraviolet absorbing agent is blended, the stability of the cosmetic can sometimes be lowered due to the influence of salts (neutralizing salts) blended together therewith.

In consideration of these circumstances, instead of using ultraviolet absorbing agents, the use of ultraviolet scattering agents, which have relatively little irritation to the skin, has been proposed. Such cosmetics have been marketed as so-called "ultraviolet absorbing agent-free" and "non-chemical" cosmetics. For example, Patent Document 2 discloses a sunscreen cosmetic that contains a hydrophobically treated zinc oxide and/or a hydrophobically treated titanium oxide as an ultraviolet scattering agent, that does not contain an organic ultraviolet absorbing agent, and that has excellent ultraviolet protection effects, emulsion stability and feeling in use. Additionally, Patent Document 3 proposes blending multiple powder components having ultraviolet scattering functions without including ultraviolet absorbing agents, such as ethylhexyl methoxycinnamate, that cause irritation upon entering the eyes.

However, in order to obtain high ultraviolet protection effects with only an ultraviolet scattering agent, a large amount of the ultraviolet scattering agent must be blended, and there are cases in which unnatural whiteness (whitening) occurs when applied to skin and the texture, such as the spreadability and the skin compatibility, are degraded.

Therefore, the achievement of higher ultraviolet protection effects while keeping the blended amounts of these ultraviolet protectants low is sought. As a result of investigation by the present inventors, they have come to understand that the ultraviolet protection effects are increased by blending particles comprising silica, silicone polymers, polymethyl methacrylate and the like.

However, as the problem of environmental contamination by plastics becomes more and more serious with each passing year, the movement towards abolishing the use of microplastic beads has accelerated in the cosmetics industry, and it is preferable to avoid using silicone polymers, polymethyl methacrylate and the like, which can be considered to be microplastic beads.

There is no established definition of microplastic beads, and they may refer only to scrubbing beads that are used in rinse-away products. However, in the present specification, they refer to solid plastic particles of polyethylene, polypropylene, polyethylene terephthalate, nylon, polyurethane, acrylates copolymers, silicone polymers or the like, having a diameter of 5 mm or less.

Meanwhile, although silica does not constitute microplastic beads, it has poor water resistance and thus, the ultraviolet protection effects tend to become lower when coming into contact with water, perspiration or the like, compared to those immediately after being applied.

RELATED ART

Patent Documents

Patent Document 1: JP 3683533 B
Patent Document 2: JP 5554308 B
Patent Document 3: JP 5813745 B

Non-patent Documents

Non-Patent Document 1: Shin-keshohingaku, second edition, edited by Takeo Mitsui, 2001, published by Nanzando, pp. 497-504.

SUMMARY OF THE INVENTION

Problem to be Solved by the Invention

The present invention was made in view of the aforementioned circumstances, and an objective of the present invention is to provide a sunscreen cosmetic that, by blending an environmentally friendly and highly water-resistant powder component instead of microplastic beads or silica, can achieve high ultraviolet protection power even when a small amount of an ultraviolet protectant is used, that moreover has the property wherein, by coming into contact with water, perspiration or the like, the ultraviolet protection effects are increased even more than those directly after being applied, and that also has an excellent texture.

Means for Solving the Problem

The present inventors performed diligent research towards solving the above-mentioned problem, as a result of which they discovered that, by blending an oil phase thickener and a prescribed wax powder into a sunscreen cosmetic containing an ultraviolet protectant, a uniform coating film having excellent water resistance is formed on the skin, thereby allowing the ultraviolet protection power to be increased, and furthermore, allowing an excellent texture to be realized. Thus, the present invention was completed.

That is, the present invention is basically a sunscreen cosmetic containing the following components (A) to (C):

(A) an oil phase thickener;

(B) an ultraviolet protectant; and (C) a wax powder having a volume-average particle size of 1 to 30 μm.

Effects of the Invention

By having the above-mentioned features, the present invention can realize a sunscreen cosmetic that can increase the ultraviolet protection power of a coating film, and that furthermore has an excellent texture.

Additionally, wax powders are more friendly to the environment than microplastic beads, which do not naturally degrade and will survive semi-permanently. Furthermore, wax powders have excellent water resistance, and the ultraviolet protection power will not be lowered by coming into contact with water, perspiration or the like, as with silica.

In addition thereto, the amount of ultraviolet protectants, which can place strain on the skin, can be kept low, therefore allowing a highly safe sunscreen cosmetic to be provided. Furthermore, high ultraviolet protection effects can be achieved even if a large amount of an ultraviolet scattering agent is not added, making the whitening and poor skin compatibility that are characteristic to ultraviolet scattering agents less likely to occur.

MODES FOR CARRYING OUT THE INVENTION

The sunscreen cosmetic of the present invention is characterized by containing (A) an oil phase thickener, (B) an ultraviolet protectant, and (C) a wax powder. Hereinafter, the components constituting the cosmetic of the present invention will be described in detail.

<(A) Oil Phase Thickener>

The (A) oil phase thickener in the present invention can be appropriately selected from among substances that are used as components providing the effect of thickening an oil phase by dissolving in an oil or swelling with an oil in a normal cosmetic or the like. For example, one or more substances selected from among dextrin fatty acid esters, sucrose fatty acid esters, glyceryl fatty acid esters, amino acid-based thickeners, acrylic polymers, solid or semi-solid hydrocarbon oils, or fatty acids or salts thereof are preferred.

Dextrin fatty acid esters are esters of dextrin or reduced dextrin with a higher fatty acid, which may be used without any particular restrictions as long as they are generally used in cosmetics. As the dextrin or reduced dextrin, one in which the average degree of sugar polymerization is 3 to 100 is preferably used. Additionally, as the constituent fatty acid in the dextrin fatty acid ester, a saturated fatty acid having 8 to 22 carbon atoms is preferably used. Specific examples include dextrin palmitate, dextrin oleate, dextrin stearate, dextrin myristate, dextrin (palmitate/2-ethylhexanoate) and the like.

As sucrose fatty acid esters, those in which the fatty acid is linear or branched, saturated or unsaturated, and having 12 to 22 carbon atoms are preferably used. Specific examples include sucrose caprylic acid esters, sucrose capric acid esters, sucrose lauric acid esters, sucrose myristic acid esters, sucrose palmitic acid esters, sucrose stearic acid esters, sucrose oleic acid esters, sucrose erucic acid esters and the like.

Glyceryl fatty acid esters are esterification reaction products obtained by reacting glycerin, a dibasic acid having 18 to 28 carbon atoms, and a fatty acid having 8 to 28 carbon atoms (excluding dibasic acids). They may be used without any particular restrictions as long as they are generally used in cosmetics. Specific examples include glyceryl (behenate/isostearate/eicosanedioate), glyceryl (behenate/eicosanedioate) and polyglyceryl-10 (behenate/eicosanedioate) and the like.

Examples of amino acid-based thickeners include dibutyl lauroyl glutamide, dibutyl ethylhexanoyl glutamide, polyamide-8, polyamide-3 and the like.

Examples of acrylic polymers include ester polymers of acrylic acid and aliphatic alcohols, and the like. For example, poly C10-30 alkyl acrylate can be favorably used.

Solid or semi-solid hydrocarbon oils are hydrocarbons that are solid or semi-solid at ambient temperature (25° C.), specific examples including vaseline, hydrogenated palm oil, hydrogenated castor oil (castor wax), hardened palm kernel oil, hardened castor oil, hydrogenated peanut oil, hydrogenated rapeseed oil, hydrogenated camellia oil, hydrogenated soybean oil, hydrogenated olive oil, hydrogenated macadamia nut oil, hydrogenated sunflower oil, hydrogenated wheat germ oil, hydrogenated rice germ oil, hydrogenated rice bran oil, hydrogenated cottonseed oil, hydrogenated avocado oil, waxes and the like.

The fatty acids are not particularly limited as long as they are of a type that can be used in cosmetics or the like, and can be selected from among fatty acids having linear or branched, saturated or unsaturated hydrocarbon groups. In particular, they are higher fatty acids that are solid at ambient temperature and that have 8 to 22 carbon atoms, for example, lauric acid, myristic acid, palmitic acid, stearic acid, behenic acid, oleic acid, isomyristic acid, isopalmitic acid or the like. Among the above, it is particularly preferable to use one or more types selected from among stearic acid, palmitic acid and behenic acid. Examples of fatty acid salts include metal salts such as sodium salts, calcium salts, magnesium salts and aluminum salts. Additionally, amide derivatives and ester derivatives of fatty acids may also be used.

The blended amount of the (A) oil phase thickener in the sunscreen composition of the present invention is adjusted so that the water content in the coating film when coming into contact with water is sufficient to cause the oil phase thickener to move within the coating film. Specifically, the blended amount of the (A) oil phase thickener may be set to be 0.3% to 4% by mass, more preferably 0.5% to 4% by mass, and even more preferably 0.5% to 3% by mass relative to the total amount of the sunscreen cosmetic. In particular, a smooth and favorable feeling to the touch can be obtained by setting the blended amount of the (A) oil phase thickener to be 4% or less, and it is thus preferable to do so.

<(B) Ultraviolet Protectant (Ultraviolet Absorbing Agent and/or Ultraviolet Scattering Agent)>

The (B) ultraviolet protectant in the present invention refers to an ultraviolet absorbing agent and/or an ultraviolet scattering agent, and one that is normally blended into cosmetics may be used.

Ultraviolet absorbing agents include, for example, benzoic acid derivatives, salicylic acid derivatives, cinnamic acid derivatives, dibenzoyl methane derivatives, $\beta\beta$-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diaryl butadiene derivatives and the like. Hereinafter, specific examples and product names will be mentioned, but there is no limitation thereto.

Examples of benzoic acid derivatives include ethyl para-aminobenzoate (PABA), ethyl-dihydroxypropyl PABA, ethylhexyl-dimethyl PABA (e.g., "Escalol 507"; ISP), glyceryl PABA, PEG-25-PABA (e.g., "Uvinul P25"; BASF), diethylamino hydroxybenzoyl hexyl benzoate (e.g., "Uvinul A Plus") and the like.

Examples of salicylic acid derivatives include homosalate ("Eusolex HMS"; Rona/EM Industries), ethylhexyl salicylate or octyl salicylate (e.g., "Neo Heliopan OS"; Haarmann & Reimer), dipropylene glycol salicylate (e.g., "Dipsal"; Scher), TEA salicylate (e.g., "Neo Heliopan TS"; Haarmann & Reimer) and the like.

Examples of cinnamic acid derivatives include octyl methoxycinnamate or ethylhexyl methoxycinnamate (e.g., "Parsol MCX"; Hoffmann-La Roche), isopropyl methoxycinnamate, isoamyl methoxycinnamate (e.g., "Neo Heliopan E1000"; Haarmaan & Reimer), cinnoxate, DEA methoxycinnamate, diisopropyl methyl cinnamate, glyceryl ethylhexanoate dimethoxycinnamate, di-(2-ethylhexyl)-4'-methoxybenzalmalonate and the like.

Examples of dibenzoyl methane derivatives include 4-tert-butyl-4'-methoxy dibenzoyl methane (e.g., "Parsol 1789") and the like.

Examples of $\beta\beta$-diphenyl acrylate derivatives include octocrylene (e.g., "Uvinul N539T"; BASF) and the like.

Examples of benzophenone derivatives include benzophenone-1 (e.g., "Uvinul 400"; BASF), benzophenone-2 (e.g., "Uvinul D50"; BASF), benzophenone-3 or oxybenzone (e.g. "Uvinul M40"; BASF), benzophenone-4 (e.g., "Uvinul MS40"; BASF), benzophenone-5, benzophenone-6 (e.g., "Helisorb 11"; Norquay), benzophenone-8 (e.g., "Spectra-Sorb UV-24"; American Cyanamid), benzophenone-9 (e.g., "Uvinul DS-49"; BASF), benzophenone-12 and the like.

Examples of benzylidene camphor derivatives include 3-benzylidene camphor (e.g., "Mexoryl SD"; Chimex), 4-methylbenzylidene camphor, benzylidene camphor sulfonic acid (e.g., "Mexoryl SL"; Chimex), camphor benzalkonium methosulfate (e.g., "Mexoryl SO"; Chimex), terephthalylidene dicamphor sulfonic acid (e.g., "Mexoryl SX"; Chimex), polyacrylamide methylbenzylidene camphor (e.g., "Mexoryl SW"; Chimex) and the like.

Examples of phenylbenzimidazole derivatives include phenylbenzimidazole sulfonic acid (e.g., "Eusolex 232"; Merck), disodium phenyldibenzimidazole tetrasulfonate (e.g., "Neo Heliopan AP"; Haarmann & Reimer) and the like.

Examples of triazine derivatives include bis-ethylhexyloxyphenol methoxyphenyl triazine (e.g., "Tinosorb S"; Ciba Specialty Chemicals), ethylhexyl triazone (e.g., "Uvinul T150"; BASF), diethylhexyl butamido triazone (e.g., "Uvasorb HEB"; Sigma 3V), 2,4,6-tris(diisobutyl-4'-amino-benzalmalonate)-s-triazine, 2,4,6-tris[4-(2-ethylhexyloxy-carbonyl)anilino]-1,3,5-triazine and the like.

Examples of phenylbenzotriazole derivatives include drometrizole trisiloxane (e.g., "Silatrizole"; Rhodia Chimie), methylene bis(benzotriazolyl tetramethylbutyl phenol) (e.g., "Tinosorb M" (Ciba Specialty Chemicals)) and the like.

Examples of anthranil derivatives include menthyl anthranilate (e.g., "Neo Heliopan MA"; Haarmann & Reimer) and the like.

Examples of imidazoline derivatives include ethylhexyl dimethoxybenzylidene dioxoimidazoline propionate and the like.

Examples of benzalmalonate derivatives include polyorganosiloxanes having benzalmalonate functional groups (e.g., Polysilicone-15; "Parsol SLX"; DSM Nutrition Japan) and the like.

Examples of 4,4-diarylbutadiene derivatives include 1,1-dicarboxy (2,2'-dimethylpropyl)-4,4-diphenylbutadiene and the like.

Among the examples of the ultraviolet absorbing agent, octocrylene, octyl salicylate and homosalate are particularly preferred, and at least one of the above is preferably included.

The ultraviolet scattering agent is not particularly limited, and for example, may be a fine-particle metal oxide such as, for example, zinc oxide, titanium oxide, iron oxide, cerium oxide and tungsten oxide.

The ultraviolet scattering agent may be non-surface-treated or may be treated with various types of hydrophobic surface treatments, but those that are hydrophobically surface-treated are preferably used. As the surface treatment agent, it is possible to use a type that is commonly used in the cosmetics field including, for example, a silicone such as dimethicone or alkyl-modified silicone, an alkoxysilane such as octyltriethoxysilane, a dextrin fatty acid ester such as dextrin palmitate, or a fatty acid such as stearic acid.

The present invention includes embodiments in which the (B) ultraviolet protectant consists only of an ultraviolet absorbing agent, embodiments in which it consists only of an ultraviolet scattering agent, and embodiments in which it includes both an ultraviolet absorbing agent and an ultraviolet scattering agent.

The blended amount of the (B) ultraviolet protectant should preferably be 5% to 40% by mass, more preferably 10% to 30% by mass, and even more preferably 10% to 20% by mass relative to the total amount of the sunscreen cosmetic. If the blended amount of the (B) ultraviolet protectant is less than 5% by mass, then sufficient ultraviolet protection effects are difficult to obtain, and even if more than 40% by mass is blended, an increase in the ultraviolet protection effects commensurate with the blended amount cannot be expected, and the stability and texture are worsened.

<(C) Wax Powder>

The (C) wax powder in the present invention is not particularly limited as long as it is a wax having a melting point of 35° C. or higher, more preferably 80° C. or higher, powdered by means of pulverization or the like, that can be blended into a cosmetic.

Although the wax constituting the wax powder is not limited to a specific wax, a wax powder from a natural source is preferred for placing less strain on the environment. Examples of such waxes include carnauba wax, rice bran wax, beeswax, biodegradable wax, microcrystalline wax and paraffin wax. Among the above, carnauba wax and rice bran wax are particularly preferred.

The method for powdering the wax is not particularly limited, and a known pulverization method may be used. Specific examples include a method of mechanically pulverizing the wax with a jet pulverizer or the like, a method of dissolving the wax in a volatile solvent and spray drying the solution, and the like.

The volume-average particle size of the wax powder should be within the range from 1 to 30 μm, more preferably within the range from 1 to 20 μm, and even more preferably within the range from 5 to 15 μm. The volume-average particle size can be measured in accordance with a standard test method for particle size distribution by laser light scattering (ASTM D4464).

The blended amount of the (C) wax powder should preferably be 0.5% to 20% by mass, more preferably 0.5% to 10% by mass, and even more preferably 1% to 5% by mass relative to the total amount of the sunscreen cosmetic. If the blended amount of the (C) wax powder is less than 0.5% by mass, then sufficient ultraviolet protection effects are difficult to obtain, and if more than 20% by mass is blended, then the texture tends to become worse.

<Optional Blended Components>

Aside from the above-mentioned components (A) to (C), components that are normally used in cosmetics may be blended into the sunscreen cosmetic of the present invention within a range not compromising the effects of the present invention. For example, gelling agents, surfactants, oils, water-based components, powder components, pH adjusters, chelating agents, preservatives, antioxidants, medicinal agents, alcohols, colorants, pigments and the like may be appropriately blended as needed.

Among the above, the stability and the texture can be further improved by blending approximately 0.1% to 2% by mass, relative to the total amount of the sunscreen cosmetic, of (D) an organically modified clay mineral as a gelling agent. Thus, it is preferable to do so.

Representative of the (D) organically modified clay mineral is a clay mineral modified by a quaternary ammonium salt type cationic surfactant, represented by the following general formula (1), which is a type of colloidal hydrated ammonium silicate having a three-layered structure.

$$(X,Y)_{2-3}(Si,Al)_4O_{10}(OH)_2Z_{1/3} \cdot nH_2O \qquad (1)$$

where X=Al, Fe(III), Mn(III) or Cr(III); Y=Mg, Fe(II), Ni, Zn or Li; and Z=K, Na or Ca.

Specific examples include dimethyl distearyl ammonium hectorite (disteardimonium hectorite), dimethylalkylammonium hectorite, benzyldimethylstearylammonium hectorite, distearyldimethylammonium chloride-treated aluminum-magnesium silicate and the like. As commercial products, Bentone 27 (benzyldimethylstearylammonium chloride-treated hectorite, manufactured by Elementis Japan) and Bentone 38 (distearyldimethylammonium chloride-treated hectorite, manufactured by Elementis Japan) are preferred.

The blended amount of the (D) organically modified clay mineral should preferably be 0.1% to 2% by mass, more preferably 0.2% to 2% by mass, and even more preferably 0.3% to 2% by mass relative to the total amount of the sunscreen cosmetic.

Additionally, it is preferable to blend, as a powder component, (E) a texture improvement powder at approximately 0.5% to 15% by mass relative to the total amount of the sunscreen cosmetic for the purposes of the texture, such as making the cosmetic even lighter to spread on the skin.

The (E) texture improvement powder is preferably a spherical powder, examples of which include cellulose powders, spherical silica, talc, mica, sericite, starch powders, biodegradable resins and the like.

Among the above, starch powders are preferable for being natural in origin and also having excellent water resistance.

The sunscreen cosmetic of the present invention can be provided in any form, but oil-based cosmetics and water-in-oil emulsion cosmetics are particularly preferred. Specific product forms include gels, emulsions, creams, lotions and the like, which can be produced by using conventional methods appropriate for each format.

In the sunscreen cosmetic of the present invention, the ultraviolet protection effects of the coating film increase upon coming into contact with water. The expression "the ultraviolet protection effects increase upon coming into contact with water" can be defined basically as follows.

First, a prescribed amount of a sample of the cosmetic is dripped onto a measurement plate, coated over a prescribed area and dried to form a coating film. The absorbance of the coating film from 400 to 280 nm is measured by means of a spectrophotometer or the like, and a pre-bath absorbance integral value of the coating film is determined with reference to the absorbance of an uncoated measurement plate.

Next, the measurement plate on which the coating film has been formed is immersed for approximately 20 minutes to 1 hour in water having a hardness of 50 to 500 at ambient temperature, then dried for approximately 10 to 30 minutes. The absorbance of the coating film is then measured and the post-bath absorbance integral value is similarly determined.

The rate of change (%) of the absorbance integral value after the water bath treatment is computed from the following equation.

Post-bath absorbance integral value change rate (%)=([post-bath absorbance integral value]/[pre-bath absorbance integral value])×100

Cases in which the absorbance integral value change rate exceeds 100% are defined as those in which the ultraviolet protection effect has increased. In the cosmetic of the present invention, the absorbance integral value change rate thereof at least exceeds 100% and is preferably 103% or higher, more preferably 105% or higher, even more preferably 110% or higher, and particularly preferably 115% or higher.

EXAMPLES

Although the present invention will be explained in further detail by providing examples below, the present invention is not limited in any way thereby. Where not otherwise noted, the blended amounts are indicated in percentage by mass relative to the total amount of the sunscreen cosmetic. Before specifically explaining each example, the evaluation methods that were employed will be explained.

<Ultraviolet Protection Power Increase Rate (SPF Boost Effect)>

Samples of each example were dripped, at a rate of 2 mg/cm², onto S plates (5×5 cm V-groove PMMA plates, SPFMASTER-PA01), spread with a finger for 60 seconds and dried for 15 minutes to form coating films. Using an uncoated plate as a control, the absorbances (400 to 280 nm) of the coating films were measured with a Hitachi U-3500 self-recording spectrophotometer, and the obtained measurement data was used to determine absorbance integral values.

$$Abs = -\log(T/T_0)$$

T: transmittance of sample, To: transmittance of uncoated plate

With Comparative Example 1, which does not include a wax powder, as the reference, the SPF boost effects were computed from the equation below and assessed on the basis of the evaluation criteria indicated below.

[SPF boost effect(%)]=([Abs of sample]/[Abs of Comparative Example 1])×100

Evaluation Criteria

A: SPF boost effect was 110% or higher
B: SPF boost effect was 100% or higher and lower than 110%
C: SPF boost effect was lower than 100%

<Post-Bath Absorbance Integral Value Change Rate (Post-Bath Abs Change Rate)>

Samples of each example were dripped, at a rate of 2 mg/cm², onto S plates (5×5 cm V-groove PMMA plates, SPFMASTER-PA01), spread with a finger for 60 seconds and dried for 15 minutes to form coating films. Using an uncoated plate as a control, the absorbances (400 to 280 nm) of the coating films were measured with a Hitachi U-3500 self-recording spectrophotometer, and the obtained measurement data was used to determine pre-bath absorbance integral values.

Next, the measured plates were fully immersed in water having a hardness of 50 to 500, and agitated (300 rpm using a 3-1 motor) in the water for 30 minutes. Thereafter, the plates were dried for about 15 to 30 minutes until the water droplets on the surfaces disappeared, the absorbances were measured again, and the post-bath light absorbance integral values were determined from the resulting measurement data.

The rates of change (%) of the post-bath absorbance integral values were computed from the equation below and assessed on the basis of the evaluation criteria indicated below.

Post-bath absorbance integral value change rate (%)=([post-bath absorbance integral value]/[pre-bath absorbance integral value])×100

Evaluation Criteria

A: Post-bath absorbance integral value change rate was 110% or higher
B: Post-bath absorbance integral value change rate was 100% or higher and lower than 110%
C: Post-bath absorbance integral value change rate was lower than 100%

<Texture>

Samples of the examples and comparative examples were actually used by ten expert panelists and evaluated regarding texture (spreadability when applied, lack of stickiness). A five-level organoleptic evaluation was performed by each panelist in accordance with the evaluation scoring criteria below, and assessments were made based on the below-mentioned evaluation criteria in accordance with the total points scored.

Evaluation Scoring Criteria

5: Very good
4: Good
3: Normal
2: Poor
1: Very poor

Evaluation Criteria

A: 40 or more total points
B: 30 to 39 total points
C: 20 to 29 total points
D: 19 or fewer total points Examples 1 to 6 and Comparative Examples 1 to 4

Water-in-oil sunscreen cosmetics having the compositions described in Table 1 and Table 2 below were prepared. The ultraviolet protection power increase rate (SPF boost effect), the post-bath absorbance integral value change rate (post-bath Abs change rate) and the texture were evaluated in accordance with the above-mentioned evaluation methods.

TABLE 1

|  | Comp Ex 1 | Ex 1 | Ex 2 | Ex 3 | Comp Ex 2 | Comp Ex 3 |
|---|---|---|---|---|---|---|
| Isododecane | 9 | 9 | 9 | 9 | 9 | 9 |
| Dimethyl silicone (6 cst) | 1 | 1 | 1 | 1 | 1 | 1 |
| Dimethicone (1.5 cst) | 15 | 15 | 15 | 15 | 15 | 15 |
| Isostearic acid | 1 | 1 | 1 | 1 | 1 | 1 |
| Polypropylene glycol (17) | 1 | 1 | 1 | 1 | 1 | 1 |
| Trimethylsiloxysilicic acid | 1 | 1 | 1 | 1 | 1 | 1 |
| PEG-9 polydimethylpolysiloxyethyl dimethicone | 1.5 | 1.5 | 1.5 | 1.5 | 1.5 | 1.5 |
| Isopropyl myristate | 2 | 2 | 2 | 2 | 2 | 2 |
| Diisopropyl sebacate | 5 | 5 | 5 | 5 | 5 | 5 |
| Dextrin palmitate | 0.5 | 0.5 | 0.5 | 0.5 | 0.5 | 0.5 |
| Sucrose tetrastearate triacetate | 1 | 1 | 1 | 1 | 1 | 1 |
| Octocrylene | 5 | 5 | 5 | 5 | 5 | 5 |
| bis-Ethylhexyloxyphenol methoxyphenyl | 1 | 1 | 1 | 1 | 1 | 1 |

TABLE 1-continued

| | Comp Ex 1 | Ex 1 | Ex 2 | Ex 3 | Comp Ex 2 | Comp Ex 3 |
|---|---|---|---|---|---|---|
| triazine | | | | | | |
| Diethylamino hydroxybenzoyl hexyl benzoate | 2 | 2 | 2 | 2 | 2 | 2 |
| Ethylhexyl salicylate | 5 | 5 | 5 | 5 | 5 | 5 |
| Dimethyldistearyl ammonium hectorite | 0.3 | — | 0.3 | 0.3 | 0.3 | 0.3 |
| Aluminum oxide stearate-treated fine-particle titanium oxide | 2 | 2 | 2 | 2 | 2 | 2 |
| Octyltriethoxysilane-treated fine-particle zinc oxide | 6 | 6 | 6 | 6 | 6 | 6 |
| Dextrin palmitate-treated fine-particle zinc oxide | 5 | 5 | 5 | 5 | 5 | 5 |
| Wax powder A | — | 5 | 5 | — | — | — |
| Wax powder B | — | — | — | 8 | — | — |
| Wax powder C | — | — | — | — | 5 | — |
| Spherical silica | — | — | — | — | — | 8 |
| Water | 25.7 | 21 | 20.7 | 17.7 | 20.7 | 17.7 |
| Ethanol | 6 | 6 | 6 | 6 | 6 | 6 |
| Glycerin | 4 | 4 | 4 | 4 | 4 | 4 |
| Total | 100 | 100 | 100 | 100 | 100 | 100 |
| SPF boost effect | Control | B | A | A | C | B |
| Post-bath Abs change rate | A | A | A | A | — | C |
| Texture | D | B | A | A | C | A |

Wax powder A: Carnauba wax with volume-average particle size of 6 to 8 μm
Wax powder B: Carnauba/rice bran wax mixture with volume-average particle size of 4 to 14 μm
Wax powder C: Carnauba wax with volume-average particle size of 100 μm
Spherical silica: Volume-average particle size of 5 μm

TABLE 2

| | Ex 4 | Ex 5 | Ex 6 | Comp Ex 4 |
|---|---|---|---|---|
| Isododecane | 9 | 9 | 9 | 9 |
| Dimethyl silicone (6 cst) | 1 | 1 | 1 | 1 |
| Dimethicone (1.5 cst) | 15 | 15 | 15 | 15 |
| Isostearic acid | 1 | 1 | 1 | 1 |
| Polypropylene glycol (17) | 1 | 1 | 1 | 1 |
| Trimethylsi 1 oxysilicic acid | 1 | 1 | 1 | 1 |
| PEG-9 polydi methyl polysiloxyethyl dimethicone | 1.5 | 1.5 | 1.5 | 1.5 |
| Isopropyl myristate | 2 | 2 | 2 | 2 |
| Diisopropyl sebacate | 5 | 5 | 5 | 5 |
| Poly C10-30 alkyl acrylate | 1 | — | — | — |
| Polyamide-8 | — | 1 | — | — |
| Glyceryl (behenate/eicosanedioate) | — | — | 0.5 | — |
| Octocrylene | 5 | 5 | 5 | 5 |
| bis-Ethyl hexyloxyphenol methoxyphenyl triazine | 1 | 1 | 1 | 1 |
| Diethylamino hydroxybenzoyl hexyl benzoate | 2 | 2 | 2 | 2 |
| Ethylhexyl salicylate | 5 | 5 | 5 | 5 |
| Dimethyldistearyl ammonium hectorite | 0.3 | 0.3 | 0.3 | — |
| Aluminum oxide stearate-treated fine-particle titanium oxide | 2 | 2 | 2 | 2 |
| Octyl triethoxysilane-treated fine-particle zinc oxide | 6 | 6 | 6 | 6 |
| Dextrin palmitate-treated fine-particle zinc oxide | 5 | 5 | 5 | 5 |
| Wax powder A | 5 | 5 | 5 | 5 |
| Water | 21.2 | 21.2 | 21.7 | 22.5 |
| Ethanol | 6 | 6 | 6 | 6 |
| Glycerin | 4 | 4 | 4 | 4 |
| Total | 100 | 100 | 100 | 100 |
| SPF boost effect | A | A | B | A |
| Post-bath Abs change rate | A | A | A | C |
| Texture | A | A | B | A |

Wax powder A: Carnauba wax with volume-average particle size of 6 to 8 μm

As indicated in Table 1 above, when an oil phase thickener and an ultraviolet protectant were contained, relatively high ultraviolet protection effects were obtained even when a wax powder was not blended, but the texture was extremely poor (Comparative Example 1).

In contrast therewith, when a wax powder having a volume-average particle size of 1 to 30 μm was blended in addition to the oil phase thickener and the ultraviolet protectant, the SPF boost effect and the texture clearly improved (Examples 1 to 3). Additionally, it was observed that the SPF boost effect and the texture were improved by further blending an organically modified clay mineral, which is a gelling agent (Example 2).

On the other hand, even when a wax powder having a volume-average particle size of 100 μm was blended, the texture mostly did not improve, and results in which the ultraviolet protection effects were conversely decreased were obtained (Comparative Example 2). Additionally, when spherical silica was blended instead of a wax powder, it was observed that the texture was excellent, but the ultraviolet protection effects were largely reduced by immersion in water (Comparative Example 3). Since Comparative Example 2 had extremely poor SPF boost effects and texture, the measurement of the post-bath Abs change rate was omitted.

As indicated in Table 2 above, excellent results in terms of SPF boost effects and texture were obtained even when the type of oil phase thickener was changed (Examples 4 to 6). Meanwhile, it was observed that the post-bath ultraviolet protection effect was significantly reduced in the case in which an oil phase thickener was not blended (Comparative Example 4).

The invention claimed is:

1. A sunscreen cosmetic containing:
   (A) an oil phase thickener;
   (B) an ultraviolet protectant;
   (C) a wax powder having a volume-average particle size of 1 to 30 μm; and
   (D) an organically modified clay mineral.

2. The sunscreen cosmetic according to claim 1, wherein the wax constituting the (C) wax powder is of one or more types selected from the group consisting of carnauba wax, rice bran wax, beeswax, biodegradable wax, microcrystalline wax and paraffin wax.

3. The sunscreen cosmetic according to claim 1, wherein the (A) oil phase thickener is of one or more types selected from among dextrin fatty acid esters, sucrose fatty acid esters, glyceryl fatty acid esters, amino acid-based thickeners, acrylic polymers, solid or semi-solid hydrocarbon oils, and fatty acids or salts thereof.

4. The sunscreen cosmetic according to claim 1, wherein a blended amount of the (A) oil phase thickener is 0.3% to 4% by mass relative to the total amount of the cosmetic.

5. The sunscreen cosmetic according to claim 1, wherein a blended amount of the (D) organically modified clay mineral is 0.1% to 2% by mass relative to the total amount of the cosmetic.

6. The sunscreen cosmetic according to claim 1, further containing (E) a texture improvement powder.

7. The sunscreen cosmetic according to claim 1, which is a water-in-oil emulsion cosmetic or an oil-based cosmetic.

* * * * *